US009548719B2

(12) United States Patent
 Sakamoto et al.

(10) Patent No.: US 9,548,719 B2
(45) Date of Patent: Jan. 17, 2017

(54) TUNING FORK TYPE PIEZOELECTRIC VIBRATION PIECE AND TUNING FORK TYPE PIEZOELECTRIC VIBRATOR

(71) Applicant: DAISHINKU CORPORATION, Kakogawa-shi, Hyogo (JP)

(72) Inventors: Yoshinobu Sakamoto, Kakogawa (JP); Satoru Ishino, Kakogawa (JP); Tomo Fujii, Kakogawa (JP)

(73) Assignee: DAISHINKU CORPORATION, Kakogawa-shi (JP)

( * ) Notice: Subject to any disclaimer, the term of this patent is extended or adjusted under 35 U.S.C. 154(b) by 0 days.

(21) Appl. No.: 14/768,831

(22) PCT Filed: May 27, 2014

(86) PCT No.: PCT/JP2014/063991
 § 371 (c)(1),
 (2) Date: Aug. 19, 2015

(87) PCT Pub. No.: WO2014/208251
 PCT Pub. Date: Dec. 31, 2014

(65) Prior Publication Data
 US 2016/0006413 A1  Jan. 7, 2016

(30) Foreign Application Priority Data

Jun. 26, 2013 (JP) .................................. 2013-134238
Jun. 28, 2013 (JP) .................................. 2013-137333

(51) Int. Cl.
 *H03H 9/21* (2006.01)
 *H03H 9/215* (2006.01)
 (Continued)

(52) U.S. Cl.
 CPC .............. *H03H 9/215* (2013.01); *A61C 1/084* (2013.01); *A61C 8/0062* (2013.01);
 (Continued)

(58) Field of Classification Search
 CPC ............ H03H 3/04; H03H 9/21; H03H 9/215; H03H 9/2468; H03H 9/2473; H03H 9/2484; H03H 9/2494; H03H 2003/026; H03H 2003/0492
 (Continued)

(56) References Cited

U.S. PATENT DOCUMENTS 8,928,422 B2 *  1/2015  Yamada ................... H03B 5/30
                                                        310/370
2009/0021120 A1   1/2009  Dalla Piazza et al.

FOREIGN PATENT DOCUMENTS

JP  2005-005896 A  1/2005
JP  2009-027711 A  2/2009
(Continued)

*Primary Examiner* — J. San Martin
(74) *Attorney, Agent, or Firm* — Marvin A. Motsenbocker; American Patent Works (57) ABSTRACT

A tuning fork type piezoelectric vibration piece 2 includes a base portion 25 in which a piezoelectric vibration substrate has a connection area with an external element, and a pair of leg portions 21, 22 projecting from a first end face of the base portion. The pair of leg portions has vibrating portions 212, 222 equipped with drive electrodes, wide weight portions 211, 221 formed at tip ends of the vibrating portions, and connecting portions 213, 223 between the vibrating portions and the weight portions. The connecting portions have widening sections whose width increases exponentially from the vibrating portions to the weight portions. The length of the widening sections is greater than their width. The weight portions have constant-width parts whose width is fixed from their connecting positions with the connecting portions. The weight portions are free of drive electrodes.

8 Claims, 7 Drawing Sheets

(51) Int. Cl.
  *H01L 41/047*  (2006.01)
  *A61C 1/08*  (2006.01)
  *A61C 8/00*  (2006.01)
  *A61C 13/107*  (2006.01)
  *A61C 13/00*  (2006.01)

(52) U.S. Cl.
  CPC ........ *A61C 8/0089* (2013.01); *A61C 13/0001* (2013.01); *A61C 13/0004* (2013.01); *H01L 41/047* (2013.01)

(58) Field of Classification Search
  USPC ......................................................... 310/370
  See application file for complete search history.

(56) References Cited

FOREIGN PATENT DOCUMENTS

| | | |
|---|---|---|
| JP | 2010-246126 A | 10/2010 |
| JP | 2011-166324 A | 8/2011 |
| JP | 2011-166325 A | 8/2011 |
| JP | 2011-239133 A | 11/2011 |
| JP | 2012-010128 A | 1/2012 |
| JP | 2012-028899 A | 2/2012 |

\* cited by examiner

FIG.9

TUNING FORK TYPE PIEZOELECTRIC VIBRATION PIECE AND TUNING FORK TYPE PIEZOELECTRIC VIBRATOR

TECHNICAL FIELD

The present invention relates to a tuning fork type piezoelectric vibration piece employed in electronic devices or the like, and also relates to a tuning fork type quartz vibrator using the same.

BACKGROUND ART

Piezoelectric vibration devices, as typically represented by piezoelectric vibrators, are widely employed in mobile telephones and other mobile communication devices. One of the piezoelectric vibration pieces employed in the piezoelectric vibrators is a tuning fork type piezoelectric vibration piece. A tuning fork type piezoelectric vibration piece has a shape of a tuning fork composed of a base portion and a pair of vibrating leg portions (hereinafter called "leg portions") extending in one direction from the base portion. A tuning fork type piezoelectric vibrator using the tuning fork type piezoelectric vibration piece is widely used as a clock source in a watch.

Recent trends toward miniaturization and improved performance for communication devices necessitate miniaturization and improved characteristics for a tuning fork type piezoelectric vibration piece. In particular, when a tuning fork type piezoelectric vibration piece is made smaller, its leg portions also become narrower and thinner. Unlike a conventional vibration piece which can suppress the influence of higher harmonics, such a small vibration piece allows higher harmonics to oscillate at a low drive level and is more likely to be adversely affected by higher harmonics. For example, in order to suppress a CI increase associated with miniaturization of a vibration piece, a tuning fork type piezoelectric vibration piece which has grooves in principal surfaces of the leg portions needs to set a greater ratio of the groove width to the leg portion width and a greater groove depth than a conventional vibration piece. In this case, banks formed between the ends of the leg portions and the grooves have a narrower width, and the thickness between the grooves in the two principal surfaces is decreased, in comparison with the conventional vibration piece. Eventually, this structure deteriorates the rigidity of the leg portions and tends to allow higher harmonic oscillation. Currently, use of a small-sized tuning fork type piezoelectric vibrator tends to cause oscillations at higher harmonic frequencies or other troubles, depending on the oscillation circuit constant or the oscillation circuit design.

For example, the tuning fork type piezoelectric vibration piece as described in Patent Literature 1 is configured to improve its electrical characteristics in order to reduce the influence of unwanted higher harmonics. According to Patent Literature 1, a tuning fork type piezoelectric vibration piece which has a base portion and a pair of leg portions projecting side by side from the base portion includes an arrangement as described below.

In the tuning fork type piezoelectric vibration piece disclosed in Patent Literature 1, each of the leg portions is composed of a vibrating portion having a drive electrode, and a weight portion formed at a tip end of the vibrating portion and having a greater width than the vibrating portion. Each leg portion is also provided with a groove which extends into the weight portion beyond the connecting position between the vibrating portion and the weight portion. Owing to the wide weight portion at the tip end of the vibrating portion, the tuning fork type piezoelectric vibration piece disclosed in Patent Literature 1 can suppress generation of higher harmonics and can stabilize the vibrational frequency, even though the vibrating portion is made shorter.

Nevertheless, in the tuning fork type piezoelectric vibration piece having such a weight portion, the rigidity of the piezoelectric vibration piece changes sharply at the connecting portion between the vibrating portion and the weight portion. Undesirably, this sharp change in rigidity destabilizes vibrations of the weight portion. To solve this problem, the tuning fork type piezoelectric vibration piece disclosed in Patent Literature 1 provides the groove at the connecting portion between the vibrating portion and the weight portion, thereby alleviating a sharp change in rigidity at the connecting portion between the vibrating portion and the weight portion and ensuring stable vibrations.

PRIOR ART REFERENCE

Patent Literature

[Patent Literature 1] JP 2011-166324 A

DISCLOSURE OF THE INVENTION

Problems to be Solved by the Invention

Patent Literature 1 suppresses generation of higher harmonics by forming a wide weight portion at the tip end of each vibrating portion, probably because the vibration node portion (hereinafter called "vibration node") which serves as a bending point of high-harmonic oscillation is displaced toward the weight portion. Nevertheless, since the leg portion-side end of the weight portion has such a tapered shape as to increase its width sharply, the mechanical strength increases sharply around the connecting portion between the vibrating portion and the weight portion, so that the vibration node is displaced merely to the vicinity of the connecting portion. In this case, displacement of the vibration node portion does not sufficiently contribute to suppression of higher harmonics.

Besides, the sharp increase in the mechanical strength at the connecting portion also causes a sharp change in the weight of the leg portion beyond the connecting portion, so that an inertia force of vibrations concentrates on the connecting portion. According to Patent Literature 1, the groove formed at the connecting portion deteriorates the mechanical strength in comparison with a connecting portion without a groove. The groove also degrades the mechanical strength and the impact resistance of a tuning fork type piezoelectric vibration piece.

Further, it is difficult to form a completely electrodeless area in a groove. To be specific, each leg portion of the tuning fork type piezoelectric vibration piece has a difference in thickness between the inside and the outside of the groove. In the case where an electrode of the tuning fork type piezoelectric vibration piece is formed by photolithography, this difference in thickness requires different focuses of exposure and complicates uniform resist exposure in the inside and the outside of the groove. If the resist is removed by simultaneous exposure of the inside and the outside of the groove, the outside of the groove is overexposed, which may cause a hollow in the side electrode or may break the electrode. Further, since the resist material is thickly deposited at the bottom of the groove, it is difficult to remove the thick resist by exposure, and eventually a residual electrode may remain in the groove. Furthermore, miniaturization of the vibration piece causes the electrode wiring in the weight portion to be thinner and narrower, so that only a slight misalignment has a high risk of causing a short circuit in a groove extension part between an electrode formed in the weight portion (such as a routing electrode, and a metal film for frequency adjustment) which does not serve as a drive electrode and a residual electrode in the groove which serves as a drive electrode.

The present invention is made in view of such circumstances, and aims to provide a tuning fork type piezoelectric vibration piece and a tuning fork type piezoelectric vibrator which is adaptable to miniaturization, which can suppress an adverse influence of higher harmonics, and which has an excellent impact resistance.

Means for Solving the Problems

In order to accomplish the above-mentioned object, the invention provides a tuning fork type piezoelectric vibration piece having following characteristics. The tuning fork type piezoelectric vibration piece includes a piezoelectric vibration substrate which has a base portion and a pair of leg portions projecting side by side from a first end face of the base portion, wherein a direction in which the leg portions project is taken as a longitudinal direction and a direction in which the leg portions are arranged side by side is taken as a widthwise direction. Each of the pair of leg portions includes: a vibrating portion having a groove extending in the longitudinal direction, and a drive electrode; a weight portion integrally formed at a tip end side of the vibrating portion and including a part whose width is greater than that of the vibrating portion; and a connecting portion between the vibrating portion and the weight portion. The drive electrode in the vibrating portion includes an inner electrode formed on an inner surface of the groove, and a side electrode formed on a side surface of the leg portion. The side electrode is opposed to the inner electrode in the widthwise direction. The connecting portion includes a widening section whose width increases exponentially from the vibrating portion to the weight portion, with a length of the widening section being longer than a width thereof. The weight portion includes a constant-width part whose width is fixed from a connecting position with the connecting portion. The weight portion is free of a drive electrode.

In order to avoid higher harmonic oscillations, a tuning fork type piezoelectric vibration piece is usually designed to increase the CI of higher harmonics by displacing vibration nodes of higher harmonics toward tip ends of the leg portions where no groove is formed in the principle surfaces. Such displacement is effected, for example, by reducing the length of grooves in the principle surfaces of the leg portions or by changing the rigidity of the leg portions. However, due to miniaturization of a vibration piece, a decrease in the groove length in the principle surfaces seriously deteriorates the CI value of the fundamental. In a vibration piece adapted to miniaturization and lower frequencies and equipped with wide weight portions at the tip ends of the leg portions, the mechanical strength of the leg portions increases sharply at the connecting portions which are in the vicinity of the boundary between the narrow vibrating portions and the wide weight portions. As a result, despite an attempt to displace the nodes of higher harmonics toward the weight portions in order to increase the CI value of higher harmonics, the nodes of higher harmonics stay at the connecting portions. Moreover, if the nodes of higher harmonics are located at an area where electrodes of opposite polarities are arranged close to each other to generate an electric field in the piezoelectric vibration substrate and to trigger bending vibrations (an area where the drive electrodes are provided), this arrangement promotes higher harmonic oscillations.

The present invention is configured such that the connecting portion includes a widening section whose width increases exponentially from the vibrating portion to the weight portion, with a length of the widening section being longer than a width thereof, that the weight portion includes a constant-width part whose width is fixed from a connecting position with the connecting portion, and that the weight portion is free of a drive electrode. Hence, the connecting portions are configured to include areas of considerable size whose width is almost the width of the vibrating portions and to increase their weight sharply toward the weight portions. Owing to this configuration, the nodes of higher harmonics can be displaced from the vibrating portions equipped with the drive electrodes to the weight-portion-side locations in the connecting portions equipped with no drive electrodes. Such displacement can increase the CI value (series resonance resistance) of unwanted higher harmonics relative to the CI value of the fundamental required to excite the tuning fork type piezoelectric vibrator, thereby ensuring the ratio of the CI values (hereinafter called "CI ratio") and suppressing higher harmonic oscillations.

The connecting portions are the points where a stress is produced. The absence of the grooves in the connecting portions reduces the risk of a crack or break in these areas and avoids deterioration of impact resistance.

In order to accomplish the above-mentioned object, the invention provides a tuning fork type piezoelectric vibration piece having following characteristics. The tuning fork type piezoelectric vibration piece includes a piezoelectric vibration substrate which has a base portion and a pair of leg portions projecting side by side from a first end face of the base portion, wherein a direction in which the leg portions project is taken as a longitudinal direction and a direction in which the leg portions are arranged side by side is taken as a widthwise direction. Each of the pair of leg portions includes: a vibrating portion having a groove extending in the longitudinal direction, and a drive electrode; a weight portion integrally formed at a tip end side of the vibrating portion and including a part whose width is greater than that of the vibrating portion; and a connecting portion between the vibrating portion and the weight portion. The drive electrode in the vibrating portion includes an inner electrode formed on an inner surface of the groove, and a side electrode formed on a side surface of the leg portion. The side electrode is opposed to the inner electrode in the widthwise direction. The connecting portion includes a widening section whose width increases from the vibrating portion to the weight portion. A principal surface of the widening section has a shape composed of a partial circumference of a circle whose radius of curvature is equal to or greater than the width of the widening section, or a shape composed of a partial circumference of an ellipse whose major axis extends in the longitudinal direction. The weight portion includes a constant-width part whose width is fixed from a connecting position with the connecting portion. The weight portion is free of a drive electrode.

In order to avoid higher harmonic oscillations, a tuning fork type piezoelectric vibration piece is usually designed to increase the CI of higher harmonics by displacing vibration nodes of higher harmonics toward tip ends of the leg portions where no groove is formed in the principle surfaces. Such displacement is effected, for example, by reducing the length of grooves in the principle surfaces of the leg portions or by changing the rigidity of the leg portions. However, due to miniaturization of a vibration piece, a decrease in the groove length in the principle surfaces seriously deteriorates the CI value of the fundamental. In a vibration piece adapted to miniaturization and lower frequencies and equipped with wide weight portions at the tip ends of the leg portions, the mechanical strength of the leg portions increases sharply at the connecting portions which are in the vicinity of the boundary between the narrow vibrating portions and the wide weight portions. As a result, despite an attempt to displace the nodes of higher harmonics toward the weight portions in order to increase the CI value of higher harmonics, the nodes of higher harmonics stay at the connecting portions. Moreover, if the nodes of higher harmonics are located at an area where electrodes of opposite polarities are arranged close to each other to generate an electric field in the piezoelectric vibration substrate and to trigger bending vibrations (an area where the drive electrodes are provided), this arrangement promotes higher harmonic oscillations.

The present invention is configured such that the connecting portion includes a widening section whose width increases from the vibrating portion to the weight portion, that a principle surface of the widening section has a shape composed of a partial circumference of a circle whose radius of curvature is equal to or greater than the width of the widening section, or a shape composed of a partial circumference of an ellipse whose major axis extends in the longitudinal direction, that the weight portion includes a constant-width part whose width is fixed from a connecting position with the connecting portion, and that the weight portion is free of a drive electrode. Hence, the connecting portions are configured to include areas of considerable size whose width is almost the width of the vibrating portions and to increase their weight sharply toward the weight portions. Owing to this configuration, the nodes of higher harmonics can be displaced from the vibrating portions equipped with the drive electrodes to the weight-portion-side locations in the connecting portions equipped with no drive electrodes. Such displacement can ensure the CI ratio and suppress higher harmonic oscillations. Eventually, this configuration prevents higher harmonics from being standing waves.

Since the widening sections are composed of a partial circumference, the connecting portions do not have a corner (a border portion) at which their width increases, and the side surfaces of the leg portions do not include any area at which a stress is produced. This configuration reduces the risk of a crack or break in these areas and enhances the impact resistance.

The connecting portions are the points where a stress is produced. The absence of the grooves in the connecting portions reduces the risk of a crack or break in these areas and avoids deterioration of impact resistance.

In order to accomplish the above-mentioned object, the invention provides a tuning fork type piezoelectric vibration piece having following characteristics. The tuning fork type piezoelectric vibration piece includes a base portion and a pair of leg portions projecting side by side from a first end face of the base portion. Each of the leg portions includes: a vibrating portion connected with the base portion and having a drive electrode; a weight portion arranged at a tip end side of the leg portion and having a greater width than the vibrating portion; and a connecting portion for connecting the vibrating portion and the weight portion in such a manner as to increase a width thereof from the vibrating portion to the weight portion. The connecting portion includes a widening section whose width increases exponentially from the vibrating portion to the weight portion. The width of the connecting portion increases in such a manner as to satisfy following conditions (a) to (c) simultaneously:

When the width of the connecting portions satisfies the conditions (a) to (c) as required by the present invention, the connecting portions are configured to include areas of considerable size whose width is almost the width of the vibrating portions and to increase their weight sharply toward the weight portions. Owing to this configuration, the nodes of higher harmonics can be displaced from the vibrating portions equipped with the drive electrodes to the weight-portion-side locations in the connecting portions equipped with no drive electrodes. Such displacement can ensure the CI ratio and suppress higher harmonic oscillations.

The connecting portions do not have a corner (a border portion) at which their width increases, and the side surfaces of the leg portions do not include any area at which a stress is produced. This configuration reduces the risk of a crack or break in these areas and enhances the impact resistance.

As recited in claim 4, a length of the groove may be not less than 55% and not greater than 65% relative to a length of the leg portions.

In the case where the grooves are formed in the leg portions and each drive electrode is composed of an inner electrode formed on an inner surface of the groove and a side electrode formed on a side surface of the leg portion, with the side electrode having an opposite polarity to the inner electrode and being opposed to the inner electrode in the widthwise direction, it is possible to enhance the electric field efficiency inside the piezoelectric vibration substrate and to improve the CI value even in a miniaturized tuning fork type piezoelectric vibration piece. In this case, longer grooves can enhance the electric field efficiency better and can reduce the CI of the fundamental greater. On the other hand, longer grooves displace the vibration nodes of higher harmonics to the grooves which contribute to oscillations, and thus deteriorate the CI of higher harmonics. For a vibration piece having a conventional weight portion, it is difficult to displace the vibration nodes beyond the grooves toward the weight portions by utilizing the weight portions. As a conventional solution for improving the CI ratio, it is desirable to set the length of the grooves to not more than 60% relative to the leg portions, or not more than 55% for a satisfactory CI ratio. In a conventional miniaturized tuning fork type piezoelectric vibration piece, a decrease in the groove length leads to serious deterioration in the CI of the fundamental, so that the piezoelectric vibration piece cannot achieve required characteristics.

According to claim 4 of the present invention, the sites where the width of the connecting portions between the grooves and the weight portions increases significantly are positioned to the weight portion side. Therefore, in addition to the function and effect as mentioned above, this configuration can secure the areas for displacing the vibration nodes of higher harmonics, and can improve the CI ratio without decreasing the length of the grooves. As a result, the length of the grooves which has to be decreased conventionally can be set to 55% to 65%, thereby decreasing the CI of the fundamental. Besides, the configuration in which the length of the grooves is not less than 55% and not greater than 65% relative to the length of the leg portions is effective in increasing the CI value of higher harmonics and ensuring the CI ratio without overly deteriorating the CI value of the fundamental. If the length of the grooves is less than 55% relative to the length of the leg portions, the CI value of the fundamental increases too much to achieve desired characteristics. If the length of the grooves is less than 65% relative to the length of the leg portions, the grooves extend into the leg portion areas including the weight portions, which is likely to sacrifice the mechanical strength and the impact resistance.

A length of the groove may be not less than 55% and not greater than 65% relative to a length of the leg portions.

In addition to the function and effect as mentioned above, the present invention according to claim 5 is configured such that the connecting portion has a second groove extending in the longitudinal direction, that a bridge having neither the groove nor the second groove is provided between the groove in the vibrating portion and the second groove in the connecting portion, and that a drive electrode is provided only in the groove in the vibrating portion. Since the bridges have a higher rigidity than the areas of the grooves and the second grooves, this configuration is equivalent to an arrangement in which the width of the leg portions is apparently widened at the bridge areas only. By the presence of the second grooves, it is also possible to decrease the rigidity of the widening sections and to facilitate displacement of vibration nodes of higher harmonics to the areas of the second grooves. Further, since the bridges can physically disconnect the second grooves from the drive electrodes, the residual electrodes inside the grooves do not contribute to oscillations, and vibration nodes of higher harmonics displaced to the second grooves do not assist higher harmonic vibrations. Thus, the nodes of higher harmonics can be displaced not only by means of the widening sections but also due to the difference in rigidity between the bridges and the second grooves. These displacement effects are effectively combined to act synergistically. In other words, it is possible to displace the nodes of higher harmonics more reliably, further away from the vibrating portions equipped with the drive electrodes, to the areas of the second grooves in the connecting portion where no drive electrode is provided. Such displacement can increase the CI value of unwanted higher harmonics relative to the CI value of the fundamental required to excite the tuning fork type piezoelectric vibrator, thereby ensuring the CI ratio and suppressing higher harmonic oscillations to a further extent.

The sites where the width of the connecting portions between the grooves and the weight portions increases significantly are positioned to the weight portion side. Therefore, in addition to the function and effect as mentioned above, this configuration can secure the areas for displacing the vibration nodes of higher harmonics, and can improve the CI ratio without decreasing the length of the grooves. As a result, the length of the grooves which has to be decreased conventionally can be set to 55% to 65%, thereby decreasing the CI of the fundamental. Besides, the configuration in which the length of the grooves is not less than 55% and not greater than 65% relative to the length of the leg portions is effective in increasing the CI value of higher harmonics and ensuring the CI ratio without overly deteriorating the CI value of the fundamental. If the length of the grooves is less than 55% relative to the length of the leg portions, the CI value of the fundamental increases too much to achieve desired characteristics. If the length of the grooves is less than 65% relative to the length of the leg portions, the grooves extend into the leg portion areas including the weight portions, which is likely to sacrifice the mechanical strength and the impact resistance.

The connecting portion may have a second groove extending in the longitudinal direction. A bridge having neither the groove nor the second groove may be provided between the groove in the vibrating portion and the second groove in the connecting portion. A drive electrode may be provided only in the groove in the vibrating portion.

In addition to the function and effect as mentioned above, the present invention is configured such that the connecting portion has a second groove extending in the longitudinal direction, that a bridge having neither the groove nor the second groove is provided between the groove in the vibrating portion and the second groove in the connecting portion, and that a drive electrode is provided only in the groove in the vibrating portion. Since the bridges have a higher rigidity than the areas of the grooves and the second grooves, this configuration is equivalent to an arrangement in which the width of the leg portions is apparently widened at the bridge areas only. By the presence of the second grooves, it is also possible to decrease the rigidity of the widening sections and to facilitate displacement of vibration nodes of higher harmonics to the areas of the second grooves. Further, since the bridges can physically disconnect the second grooves from the drive electrodes, the residual electrodes inside the grooves do not contribute to oscillations, and vibration nodes of higher harmonics displaced to the second grooves do not assist higher harmonic vibrations. Thus, the nodes of higher harmonics can be displaced not only by means of the widening sections but also due to the difference in rigidity between the bridges and the second grooves. These displacement effects are effectively combined to act synergistically. In other words, it is possible to displace the nodes of higher harmonics more reliably, further away from the vibrating portions equipped with the drive electrodes, to the areas of the second grooves in the connecting portion where no drive electrode is provided. Such displacement can increase the CI value of unwanted higher harmonics relative to the CI value of the fundamental required to excite the tuning fork type piezoelectric vibrator, thereby ensuring the CI ratio and suppressing higher harmonic oscillations to a further extent.

As recited in claim 7, the connecting portion may include a widening section whose width increases exponentially from the vibrating portion to the weight portion. The width of the connecting portion may increase in such a manner as to satisfy following conditions (a) to (c) simultaneously:

(a) the widening section is composed of a smooth curve, and monotonically increases the width of the connecting portion from the vibrating portion to the weight portion;

(b) a rate of increase in the width of the connecting portion rises as the connecting portion is more distant from a boundary with the vibrating portion; and (c) the rate of increase in the width of the connecting portion is zero at the boundary between the vibrating portion and the connecting portion.

In order to accomplish the above-mentioned object, the invention provides a tuning fork type piezoelectric vibration piece having following characteristics. The tuning fork type piezoelectric vibration piece includes a piezoelectric vibration substrate which has a base portion and a pair of leg portions projecting side by side from a first end face of the base portion, wherein a direction in which the leg portions project is taken as a longitudinal direction and a direction in which the leg portions are arranged side by side is taken as a widthwise direction. Each of the pair of leg portions includes: a vibrating portion having a first groove extending in the longitudinal direction, and a drive electrode; a weight portion integrally formed at a tip end side of the vibrating portion and including a part whose width is greater than that of the vibrating portion; and a connecting portion between the vibrating portion and the weight portion. The drive electrode which is formed only in the vibrating portion includes an inner electrode formed on an inner surface of the first groove, and a side electrode formed on a side surface of the leg portion. The side electrode is opposed to the inner electrode in the widthwise direction. The connecting portion has a second groove extending in the longitudinal direction. A bridge having neither the first groove nor the second groove is provided between the first groove in the vibrating portion and the second groove in the connecting portion. The bridge is located in the vibrating portion.

The connecting portions do not have a corner (a border portion) at which their width increases, and the side surfaces of the leg portions do not include any area at which a stress is produced. This configuration reduces the risk of a crack or break in these areas and enhances the impact resistance.

The connecting portion may include a widening section whose width increases exponentially from the vibrating portion to the weight portion. The width of the connecting portion may increase in such a manner as to satisfy following conditions (a) to (c) simultaneously:

Effects of the Invention

As described above, the present invention can provide a tuning fork type piezoelectric vibration piece and a tuning fork type piezoelectric vibrator which is adaptable to miniaturization, which avoids an adverse influence of higher harmonics, and which has an excellent impact resistance.

MODE FOR CARRYING OUT THE INVENTION

Embodiment 1

Figure 1:
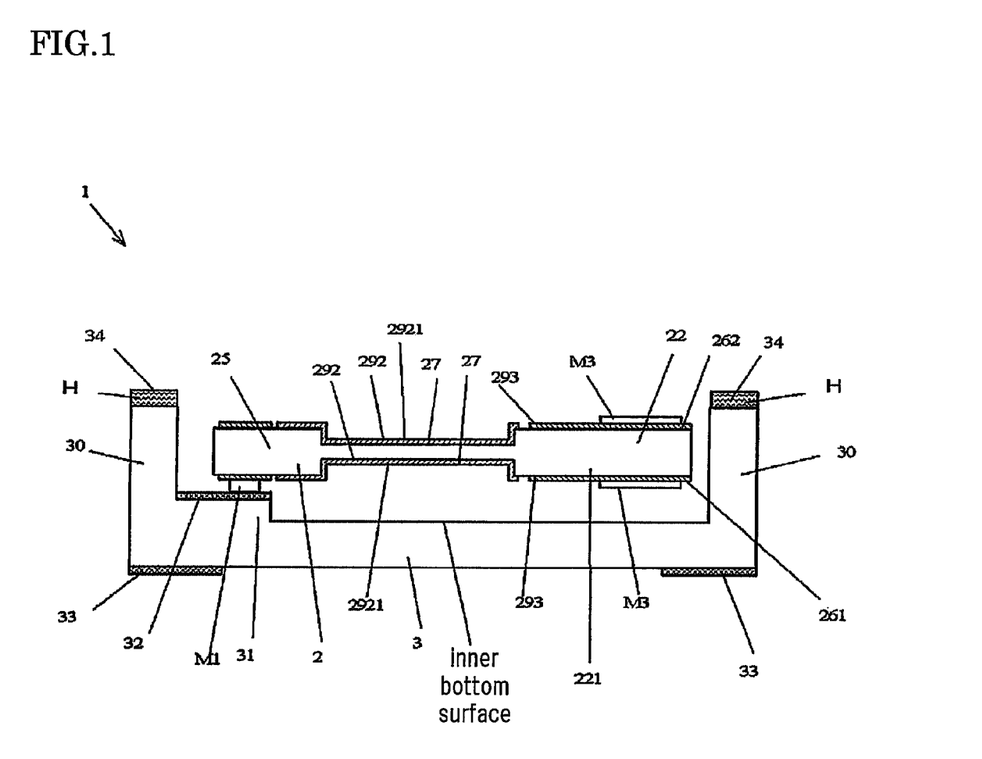
FIG. 1 is a schematic cross section of a tuning fork type quartz vibrator according to Embodiment 1 of the present invention.

Hereinafter, a tuning fork type quartz vibrator is described as an example, with reference to the attached drawings. A tuning fork type quartz vibrator 1 used in this embodiment has a housing composed of a base 3 and a lid (not shown) bonded by a sealing member H. Specifically, a tuning fork type quartz vibration piece 2 is connected to an electrode pad 32 of the open-top base with the interposition of a first metal film M1 such as a plated bump, and the lid covers the opening of the base with the sealing member H. In this embodiment, the nominal frequency of the tuning fork type quartz vibrator is 32.768 kHz. This nominal frequency is a mere example, and other frequencies are also applicable.

In addition to the function and effect as mentioned above, the configuration of the present invention exhibits the following function and effect. The connecting portions are configured to include areas of considerable size whose width is almost the width of the vibrating portions and to increase their weight sharply toward the weight portions. Owing to this configuration, the nodes of higher harmonics can be displaced from the vibrating portions equipped with the drive electrodes to the weight-portion-side locations in the connecting portions equipped with no drive electrodes. Such displacement can ensure the CI ratio and suppress higher harmonic oscillations.

The perimeter of the dike 30 of the base 3 is circumferentially provided with a metal film layer (constituting a part of the sealing member H) 34. In an example where the base 3 is made of a ceramic material, the electrode pads 32, 32, the terminal electrodes 33, 33, and the metal film layer 34 are configured, for example, by three layers in order of tungsten-nickel-gold from bottom to top. The tungsten layer is integrally formed by metallization during ceramic firing, and each of the nickel layer and the gold layer is formed by plating. The tungsten layer may be replaced with a molybdenum layer.

Further, the tuning fork type piezoelectric vibration piece as configured above is applicable to a tuning fork type piezoelectric vibrator in which the tuning fork type piezoelectric vibration piece is hermetically sealed inside a housing of the tuning fork type piezoelectric vibrator. With the above-mentioned tuning fork type piezoelectric vibration piece being bonded on a holding part inside the housing, the tuning fork type piezoelectric vibrator exhibits similar functions and effects.

Although not shown, the tuning fork type quartz vibration piece 2 is manufactured as a matrix of multiple tuning fork type quartz vibration pieces (piezoelectric vibration substrates) formed collectively on a single quartz crystal wafer composed of an anisotropic quartz Z-plate. The outer shape of the tuning fork type quartz vibration piece 2 is collectively formed by photolithography, for example, by wet etching using a resist mask or a metal film mask.

Figure 2:
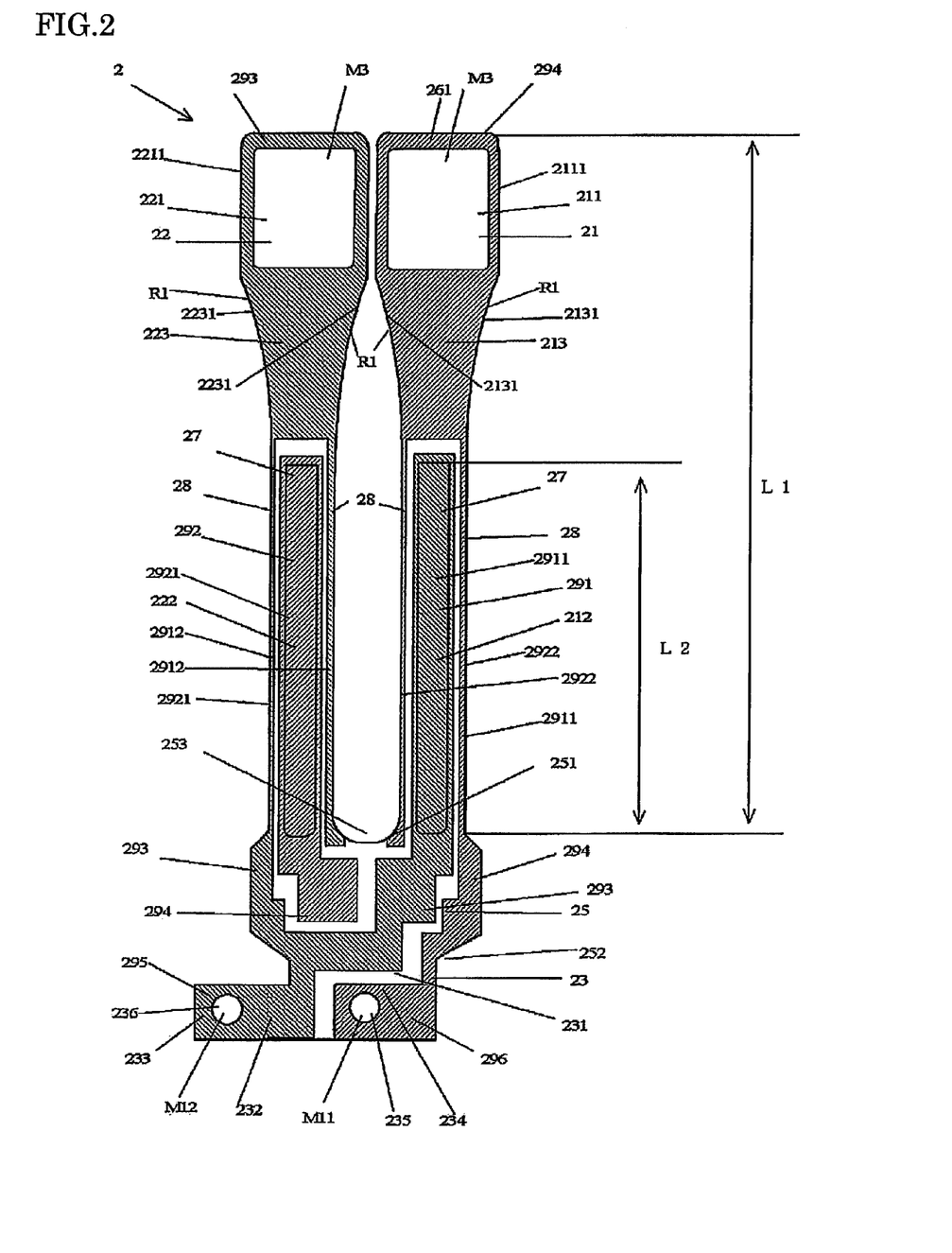
FIG. 2 is a plan view of a principle surface of a tuning fork type quartz vibration piece according to Embodiment 1 of the present invention.

As illustrated in FIG. 2, the external shape of the tuning fork type quartz vibration piece (piezoelectric vibration substrate) 2 is composed of a pair of leg portions (a first leg portion 21 and a second leg portion 22) as vibrating elements, a branching portion 253 between the leg portions 21, 22, a joint portion 23 for making an external connection (the electrode pads 32, 32 of the base 3 in this embodiment), and a base portion 25 from which the first leg portion 21, the second leg portion 22, and the joint portion 23 project. The first leg portion 21 and the second leg portion 22 project side by side from a first end face 251 of the base portion 25, with the interposition of the branching portion 253. The branching portion 253 in this embodiment is provided at a widthwise middle position (central area) in the first end face 251. For the purpose of description, the direction in which the first leg portion 21 and the second leg portion 22 project is taken as a longitudinal direction (the Y-axis direction in this embodiment), and the direction in which the first leg portion 21 and the second leg portion 22 are arranged side by side is taken as a widthwise direction (the X-axis direction in this embodiment).

According to this embodiment, following electrodes are formed integrally and simultaneously on the front and back principle surfaces (a first principle surface 261 and a second principle surface 262) of the tuning fork type quartz vibration piece (piezoelectric vibration substrate) 2. Specifically, a pair of first and second drive electrodes 291, 292 of different potentials, extraction electrodes 293, 294 routed from the first and second drive electrodes 291, 292 in order to electrically connect the first and second drive electrodes 291, 292 with the electrode pads 32, 32, and connection electrodes 295, 296 each having a metal film M1 at a tip end thereof. In this embodiment, the extraction electrodes 293, 294 indicate the electrode patterns routed from the first and second drive electrodes 291, 292. The connection electrodes 295, 296 are formed at joint portions in the tip ends (lead-out ends) of the extraction electrodes 293, 294.

In the tuning fork type quartz vibration piece 2, the first and second drive electrodes 291, 292, the extraction electrodes 293, 294, and the connection electrodes 295, 296 are thin films formed by metal deposition, with a chromium (Cr) layer on the first and second leg portions 21, 22 and a gold (Au) layer on the chromium layer. These thin films are integrally and simultaneously formed on the entire surface of the substrate by vacuum vapor deposition, sputtering or like method, and then shaped as desired by metal etching by photolithography. The first and second drive electrodes 291, 292 and the extraction electrodes 293, 294, which are composed in order of chromium-gold (Cr—Au), may be also composed of in order of chromium-silver (Cr—Ag), chromium-gold-chromium (Cr—Au—Cr), chromium-silver-chromium (Cr—Ag—Cr), for example.

The first and second leg portions 21, 22 include vibrating portions 212, 222 having grooves 27 (to be described) extending in the longitudinal direction and drive electrodes, weight portions 211, 221 provided at tip ends of the vibrating portions 212, 222 and including parts whose width is greater than that of the vibrating portions, and connecting portions 213, 223 between the vibrating portions 212, 222 and the weight portions 211, 221. The tip ends of the leg portions have a high sensitivity suitable to serve as frequency adjustment areas. Hence, the wide weight portions 211, 221 can increase the high-sensitivity area, so that the weight portions 211, 221 (tip areas) can serve more effectively in frequency adjustment. Generally, it is possible to lower the frequency by making the tip ends of the leg portions wider and heavier. However, if the tuning fork type quartz vibration piece 2 is made smaller without the wide weight portions, the leg portions must be made narrower. This arrangement is disadvantageous in formation of the grooves and the drive electrodes, and degrades the CI value. In contrast, the wide weight portions as taught in the present embodiment can ensure a sufficient width for the leg portions, can enhance the CI-value characteristics, and can be useful in lowering the frequency.

The first drive electrode 291 is formed on both principle surfaces (the first principle surface 261 and the second principle surface 262) of the vibrating portion 212 in the first leg portion 21, and on both side faces 28 of the vibrating portion 222 in the second leg portion 22. Similarly, the second drive electrode 292 is formed on both principle surfaces (the first principle surface 261 and the second principle surface 262) of the vibrating portion 222 in the second leg portion 22, and on both side faces 28 of the vibrating portion 212 in the first leg portion 21.

The vibrating portions 212, 222 have closed-bottom grooves 27 in the first and second principle surfaces 261, 262, respectively. A part of the first and second drive electrodes 291, 292 is also formed inside the grooves 27. Therefore, even when the size of the tuning fork type quartz vibration piece 2 is reduced, it is possible to suppress vibration loss in the first and second leg portions 21, 22 and to keep a low CI value (series resonant resistance value). Desirably, the length of each groove 27 in the longitudinal direction (L2) is not less than 55% and not greater than 65% relative to the length of the leg portions 21, 22 in the longitudinal direction (L1). For example, L2 is 60% in this embodiment.

In the present invention, the drive electrodes at least include inner electrodes formed on the inner surfaces of the grooves and side electrodes formed on the side surfaces of the leg portions, the side electrodes having an opposite polarity to the inner electrodes and being opposed to the inner electrodes in the widthwise direction. Owing to the close arrangement of these opposite-polarity electrodes in the vibrating portions, the drive electrodes trigger a field-effect inside the quartz vibration piece. Based on this definition, the drive electrodes do not include an extraction electrode or the like for the purpose of wiring. Namely, the drive electrode in the vibrating portion 212 generally includes a group of peripheral electrodes composed of first drive electrodes 291, 291 formed on both principle surfaces of the first leg portion 21 (FIG. 2 only shows the one on the first principle surface 261), inner electrodes 2911, 2911 formed on the inner surfaces of the grooves 27, 27 in the same principle surfaces as the first drive electrodes and having the same polarity as the first drive electrodes (FIG. 2 only shows the one on the first principle surface 261), and side electrodes 2922, 2922 formed on both side surfaces of the first leg portion 21, having an opposite polarity to the inner electrodes 2911, 2911 and being opposed to the inner electrodes 2911, 2911 in the widthwise direction. The drive electrode in the vibrating portion 222 generally includes a group of peripheral electrodes composed of second drive electrodes 292, 292 formed on both principle surfaces of the second leg portion 22 (FIG. 2 only shows the one on the first principle surface 261), inner electrodes 2921, 2921 formed on the inner surfaces of the grooves 27, 27 in the same principle surfaces as the second drive electrodes and having the same polarity as the second drive electrodes (FIG. 2 only shows the one on the first principle surface 261), and side electrodes 2912, 2912 formed on both side surfaces of the second leg portion 22, having an opposite polarity to the inner electrodes 2921, 2921 and being opposed to the inner electrodes 2921, 2921 in the widthwise direction.

The weight portions 211, 221 have curved corners, and also have constant-width areas 2111, 2211 in which the width of the weight portions is fixed from the terminal ends of the connecting portions 213, 223 to the tip ends thereof. In these weight portions, at least the constant-width areas 2111, 2211 are provided only with the extraction electrodes 293, 294 to be described later and not provided with a drive electrode. The curved corners of the weight portions 211, 221 can prevent a contact with a dike or the like under an external force or in other occasions. The constant-width areas 2111, 2211 can enlarge high-sensitive areas which are effective in frequency adjustment at the tip ends of the leg portions.

In the weight portion 211 of the first leg portion 21 and the weight portion 221 of the second leg portion 22, the extraction electrodes 293, 294 are formed substantially entirely on the two principle surfaces (the first principle surface 261 and the second principle surface 262) and on both of the side surfaces 28. Since the weight portions 211, 221 are not provided with a drive electrode, it is possible to avoid close arrangement of opposite-polarity electrodes, to avoid a short circuit, and to simplify the fabrication.

Figure 3:
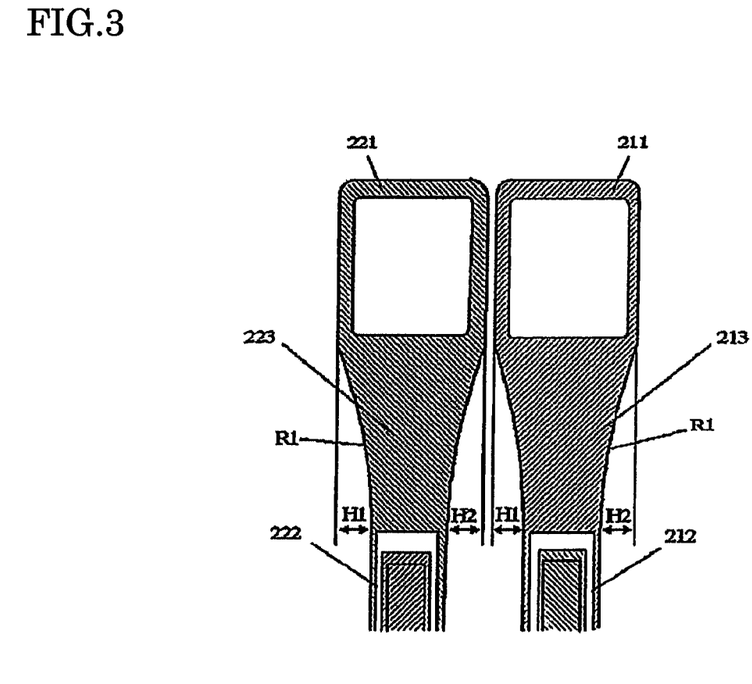
FIG. 3 is an enlarged partial plan view of the leg portions of the tuning fork type quartz vibration piece according to Embodiment 1 of the present invention.
Figure 4:
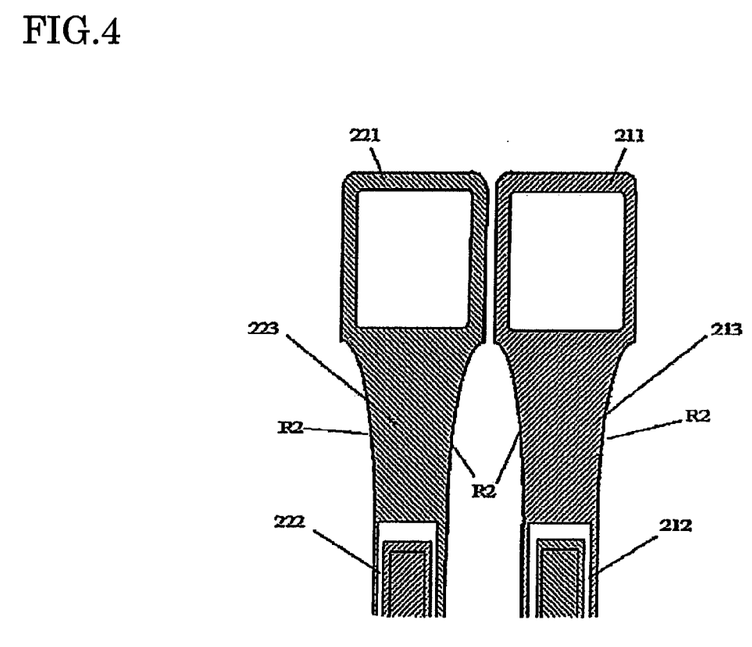
FIG. 4 is an enlarged partial plan view of the leg portions of the tuning fork type quartz vibration piece according to another mode of Embodiment 1 of the present invention.

The connecting portions 213, 223 have widening sections 2131, 2231 whose width increases exponentially from the vibrating portions 212, 222 to the weight portions 211, 221. The length of these widening sections 2131, 2231 is longer than their width. This configuration is described more specifically with reference to FIG. 3. With regard to the shape of the principle surfaces of the tuning fork type quartz vibration piece 2, the width of the weight portions 211, 221 is greater than the width of the vibrating portions 212, 222 by a widening width H1, H2 (which is the width of the widening sections 2131, 2231). Each of the widening sections 2131, 2231 is composed of a partial circumference of a circle whose radius of curvature is not less than the total of the widening widths H1 and H2. In this embodiment, for example, each of the widening sections 2131, 2231 is composed of a partial circumference R1 of a circle whose radius of curvature is eight times as large as the total of the widening widths H1 and H2. Instead of the circular part R1, the widening sections 2131, 2231 may be composed of a partial circumference R2 of a quarter ellipse whose major axis extends in the projection direction of the leg portions, as shown in FIG. 4.

In the present invention, the exponential increase of the width of the connecting portions 213, 223 satisfies the following conditions (a) to (c) simultaneously.

(a) Each widening section is composed of a smooth curve, and monotonically increases the width of the connecting portion from the vibrating portion to the weight portion.

(b) The rate of increase in the width of the connecting portion rises as the connecting portion is more distant from the boundary with the vibrating portion (with a proviso that the direction from the vibrating portion to the weight portion in the longitudinal direction or Y-axis direction is positive, and that the width-increasing direction in the widthwise direction or X-axis direction is positive, the slope of a tangent at the widening section (dX/dY) increases monotonically from the vibrating portion to the weight portion.)

(c) The rate of increase in the width of the connecting portion is zero at the boundary between the vibrating portion and the connecting portion. (The slope of a tangent at the boundary between the vibrating portion and the connecting portion is zero.)

Owing to the widening sections 2131, 2231 whose width increases exponentially from the vibrating portions 212, 222 to the weight portions 211, 221, the tuning fork type quartz vibration piece 2 according to this embodiment exhibits following effects.

The first effect results from the fact that the width of the widening sections 2131, 2231 increases exponentially. In comparison with Patent Literature 1 in which the weight portion has a tapered shape at the leg portion-side end, the present embodiment avoids a sharp increase in mechanical strength in the vicinity of the connecting positions between the vibrating portions 212, 222 and the connecting portions 213, 223. Hence, the vibration nodes do not stay in the vicinity of the connecting positions, and can be displaced further toward the weight portions 211, 221. Among the tuning fork type quartz vibration pieces which have leg portions of the same length, the one in which vibration nodes are displaced further toward the weight portions can better improve the effect of suppressing higher harmonics.

The second effect results from the fact that, in comparison with Patent Literature 1, the present embodiment avoids a sharp increase in mechanical strength in the vicinity of connecting positions between the vibrating portions 212, 222 and the connecting portions 213, 223. Although Patent Literature 1 requires grooves at the connecting positions between the vibrating portions and the weight portions, the present embodiment can omit such grooves, and can still ensure stable vibrations by avoiding concentration of an inertia force of vibrations at the connecting positions. Eventually, the present embodiment can avoid deterioration of mechanical strength due to the grooves as taught in Patent Literature 1, and can ensure a sufficient strength for a tuning fork type piezoelectric vibration piece.

The third effect results from the fact that, in comparison with Patent Literature 1, the present embodiment can omit the grooves as taught in Patent Literature 1, and can still ensure stable vibrations by avoiding concentration of an inertia force of vibrations at the connecting positions. In the case of Patent Literature 1 where a (drive) electrode formation area and an electrode-free area are formed in one groove, an electrode which cannot be removed completely from the electrode-free area causes a short circuit with a drive electrode. In contrast, the tuning fork type quartz vibration piece 2 according to the present embodiment can prevent this problem by omitting a groove at the connecting position between the vibrating portion and the weight portion.

In the connecting portion 213 of the first leg portion 21 and the connecting portion 223 of the second leg portion 22, the extraction electrodes 293, 294 are formed substantially entirely on the two principle surfaces (the first principle surface 261 and the second principle surface 262) and on both of the side surfaces 28. Since the connecting portions 213, 223 are not provided with a drive electrode, it is possible to avoid close arrangement of opposite-polarity electrodes, to avoid a short circuit, and to simplify the fabrication.

Further, on the first principle surface 261, adjustment metal films (frequency adjustment weights) M3 are provided at least on top surfaces of the extraction electrodes 293, 294, at the constant-width area 2111 of the weight portion 211 in the first leg portion 21 and at the constant-width area 2211 of the weight portion 221 in the second leg portion 22. To adjust the frequency of the tuning fork type quartz vibration piece 2, the mass of the adjustment metal films (frequency adjustment weights) M3 is reduced by laser beam or other beam irradiation or by ion milling or other ion etching. Formation of the adjustment metal films (frequency adjustment weights) M3 is not limited to the above-described manner. In addition to the constant-width area 2111 of the weight portion 211 in the first leg portion 21 and the constant-width area 2211 of the weight portion 221 in the second leg portion 22, the adjustment metal films (frequency adjustment weights) M3 may be also formed on the entirety of the weight portion 211 and a part of the connecting portion 213 in the first leg portion 21 as well as on the entirety of the weight portion 221 and a part of the connecting portion 213 in the second leg portion 22, with a slightly smaller area than the extraction electrodes formed in the same parts. The adjustment electrode metal films (frequency adjustment weights) M3 may be formed on the two principle surfaces (the first principle surface 261 and the second principle surface 262) as in this embodiment, or may be formed only on the second principle surface 262 which faces the opening of the base.

The adjustment metal films M3 are formed, for example, by providing adjustment metal film formation portions in a desired shape at corresponding sites on the extraction electrodes 293, 294 by photolithography, and plating the adjustment metal films M3 at the adjustment metal film formation portions by electrolytic plating or like technique. Optionally, the metal films may be annealed thereafter. In practice, it is more preferable to form these adjustment metal films by plating simultaneously in the same step as the plating of the above-mentioned metal films M1 (M11, M12).

The base portion 25 is vertical line symmetry in plan view, and is wider than the vibrating portions 212, 222, as illustrated in FIG. 2. The base portion 25 has a gradually tapered shape in the vicinity of a second end face 252, such that its width gets narrower from a first end face 251 to the second end face 252. Owing to this configuration, leaking vibration generated by vibrations of the vibrating portions composed of the first and second leg portions 21, 22 can be attenuated by the second end face 252, and transmission of the leaking vibration to the joint portion 23 can be suppressed. This is preferable for further reduction in acoustic leakage (vibration leakage). The gradually narrowing configuration is not limited to the tapered shape, but may be a stepped shape or a curved shape.

As shown in FIG. 2 and FIG. 3, the joint portion 23 electromechanically connects the extraction electrodes 293, 294 to external electrodes (the term "external" should be understood in the context of the present invention, and the term "external electrodes" indicates the electrode pads 32, 32 of the base 3 in this embodiment). Specifically, while the first and second leg portions 21, 22 project from the first end face 251 of the base portion 25, the joint portion 23 projects from a widthwise middle position (central area) in the second end face 252 opposite to the first end face 251. In other words, the joint portion 23 projects from a position opposite to the branching portion 253 between the first and second leg portions 21, 22.

Particularly, the joint portion 23 in this embodiment is composed of a shorter portion 231 and a longer portion 232. The shorter portion 231 projects vertically in plan view from the second end face 252 of the base portion 25, and is narrower than the second end face 252. The longer portion 232 adjoins a tip end of the shorter portion 231, is bent perpendicularly in plan view at the tip end of the shorter portion 231, and extends in a widthwise direction of the base portion 25. A tip end 233 of the joint portion 23 is oriented in the widthwise direction of the base portion 25. Namely, the joint portion 23 has an L-shape in plan view, bent at a bent portion 234 which corresponds to the tip end of the shorter portion 231. Since the shorter portion 231 is narrower than the second end face 252 of the base portion 25, this configuration further enhances the effect of suppressing vibration leakage.

The first principle surface 261 in the joint portion 23 includes a first joint region 235 and a second joint region 236 for external connection. The first joint region 235 is formed in a part of the bent portion 234 of the joint portion 23 having an L-shape in plan view, on an extension of a line along the widthwise center of the base portion 25 (at a widthwise middle position in the shorter portion 231 of the joint portion 23). The second joint region 236 is formed in a part of a tip end of the longer portion 232 which constitutes the tip end 233 of the joint portion 23 having an L-shape in plan view. The first joint region 235 is provided with a connection electrode 296 (a lead-out end of the extraction electrode 294) which is routed from the second drive electrode 292 to be described later, via the extraction electrode 294, to an end (a first end) of the shorter portion 231. The second joint region 236 is provided with a connection electrode 295 (a lead-out end of the extraction electrode 293) routed from the first drive electrode 291 to be described later, via the extraction electrode 293, to an end (a first end) of the longer portion 232.

This configuration can suppress vibration leakage (acoustic leakage) more efficiently without increasing the length of the joint portion 23. In particular, the first joint region 235 of the joint portion 23 for external connection is provided on an extension of the line along the widthwise center of the base portion 25. Therefore, the narrow tapered portion near the second end face 252 of the base portion 25 can not only suppress acoustic leakage and but also cancel even a slight acoustic leakage in the widthwise direction. Then, the first joint region 235 can make an electrical and mechanical connection, as one of the poles, at the bent portion 234 where acoustic leakage is suppressed more efficiently. The second joint region 236 of the joint portion 23 for external connection can make an electrical and mechanical connection, as the other pole having an opposite polarity, at the tip end 233 that is not affected by acoustic leakage, stress or external force.

Additionally, metal films M1 (M11, M12) are provided on top surfaces of the connection electrodes 295, 296. The metal films M1 (M11, M12) are plated bumps which have a greater surface roughness and a smaller plane area than the connection electrodes 295, 296. The metal films M1 (M11, M12) have a circular shape in plan view, with a thickness of, for example, about 5 to 20 μm, a diameter of about 50 μm, and a plane area of about 1962.5 μm². After ultrasonic bonding (after FCB), at least the metal films M1 (M11, M12) spread in a planar direction in a squeezed state to be about half as thick as the original. If the metal films M1 (M11, M12) are thinner than 5 μm, the gap between the connection electrodes 295, 296 of the tuning fork type quartz vibration piece 2 and the electrode pads 32, 32 of the base 3 is so small as to give an adverse influence on electrical characteristics of the tuning fork type quartz vibrator. If the metal films M1 (M11, M12) are thicker than 20 μm, the metal films are likely to cause inclination or misalignment of the tuning fork type quartz vibration piece 2 and to make the bonding strength uneven. The planar shape of the metal films M1 (M11, M12) as plated bumps may be freely arranged in accordance with the planar shape of the connection electrodes and the like, including a circular shape such as a circle or an ellipse and a polygonal shape such as a rectangle or a square.

To form the metal films M1 (M11, M12) on the joint portion 23, metal film formation areas (not shown) (masks having windows whose plane area is smaller than that of the connection electrodes 295, 296) are formed on the first and second joint regions 235, 236 of the joint portion 23, in a desired shape (circular windows in this embodiment) by photolithography. Then, the metal films M1 (M11, M12) are plated on the metal film formation areas by electrolytic plating or the like. Optionally, the metal films may be annealed thereafter.

Next, the tuning fork type quartz vibration pieces 2 configured in the above-described manner are subjected to rough frequency adjustment. In the state of the wafer as mentioned above, the frequency of each tuning fork type quartz vibration piece 2 is measured and roughly adjusted by reducing the adjustment metal films M3 by beam irradiation or by adding the adjustment metal films M3 by partial vapor deposition.

After the rough frequency adjustment, each tuning fork type quartz vibration piece 2 is picked up from the wafer and mounted on the base 3 by FCB, by ultrasonically bonding the electrode pads 32, 32 of the base 3 with the metal films M1 (M11, M12) formed on the top surfaces of the connection electrodes 295, 296 on the first principle surface 261.

The tuning fork type quartz vibration piece 2 mounted on the base 3 is then subjected to final frequency adjustment. The frequency of the tuning fork type quartz vibration piece 2 is measured again and finely adjusted by reducing the adjustment metal films M3 by beam irradiation or ion etching.

After the final frequency adjustment, a lid (not shown) is bonded via the sealing member H onto the base 3 which mounts the tuning fork type quartz vibration piece 2, by heat-fusion bonding or like methods. Thereby, the tuning fork type quartz vibration piece 2 is hermetically sealed inside the housing composed of the base 3 and the lid (not shown). Methods for this hermetic sealing include seam welding, beam welding, atmospheric heating, and the like.

Next, a modified example of the present invention is described with reference to FIG. 5 by mainly focusing on differences from the above-described embodiment. In the modified example of the present invention, the connecting portions 213, 223 have closed-bottom second grooves 271 which extend in the longitudinal direction. Bridges 272 lie between the closed-bottom grooves 27 in the vibrating portions 212, 222 and the second grooves 271 in the connecting portions 213, 223. In this example, the bridges 272 are unetched areas in the tuning fork type quartz vibration piece (piezoelectric vibration substrate), and have the same thickness as areas excluding the grooves 27 and the second grooves 271 in the leg portions 21, 22. In the connecting portion 213 of the first leg portion 21 and the connecting portion 223 of the second leg portion 22, the extraction electrodes 293, 294 are formed substantially entirely on the two principle surfaces (the first principle surface 261 and the second principle surface 262) and on both of the side surfaces. The extraction electrodes 293, 294 are also formed inside the second grooves.

Figure 5:
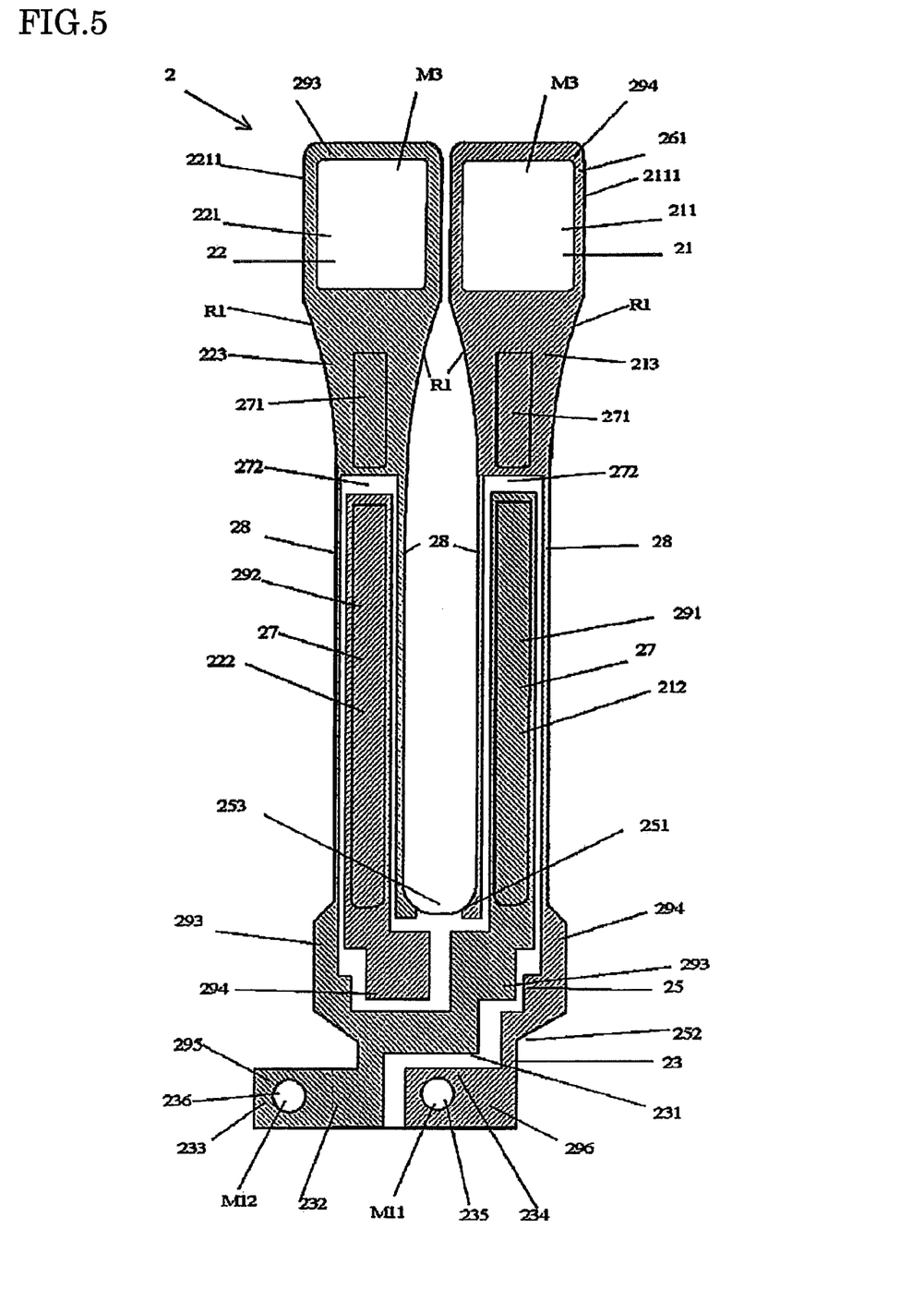
FIG. 5 is a plan view of a principle surface of a tuning fork type quartz vibration piece according to a modified example of Embodiment 1 of the present invention.

In the modified example shown in FIG. 5, the second grooves 271 occupy only a part of the connecting portions 213, 223. However, according to the characteristics, the second grooves 271 may be extended into either of the weight portions 211, 221 or the vibrating portions 212, 222, or into both of the weight portions 211, 221 and the vibrating portions 212, 222. The top surfaces of the second grooves may be free of an extraction electrode, or may be provided with both the extraction electrodes and the adjustment metal films M3 formed on the extraction electrodes. As far as this modified example is concerned, at least two or more of these variations may be combined. It should be noted, however, the second grooves are not provided with a drive electrode which triggers a field-effect inside the quartz vibration piece due to close arrangement of opposite-polarity electrodes.

The above-described arrangement can provide a tuning fork type piezoelectric vibration piece and a tuning fork type piezoelectric vibrator, which allows miniaturization of the tuning fork type quartz vibration piece 2 without an adverse influence due to higher harmonics and which has an excellent impact resistance.

The connecting portions 213, 223 have widening sections 2131, 2231 whose width increases exponentially from the vibrating portions 212, 222 to the weight portions 211, 221. The length of these widening sections 2131, 2231 is longer than their width. The weight portions 211, 221 have constant-width areas 2111, 2211 whose width is fixed from the terminal ends of the connecting portions 213, 223 to the tip ends of the weight portions 211, 221. The weight portions 211, 221 are provided with the extraction electrodes 293, 294 only. Since the weight of the tuning fork type piezoelectric vibration piece increases sharply toward the weight portions 211, 221, nodes of unwanted higher harmonics other than the fundamental can be displaced from the vibrating portions 212, 222 having the drive electrodes toward the weight portions 211, 221 having no drive electrode. Such displacement can increase the CI value (series resonance resistance) of unwanted higher harmonics relative to the CI value of the fundamental required to excite the tuning fork type piezoelectric vibrator, thereby ensuring the ratio of the CI values (hereinafter called "CI ratio") and suppressing higher harmonic oscillations.

The connecting portions 213, 223 are the points where a stress is produced. The absence of the grooves 27 in the connecting portions 213, 223 reduces the risk of a crack or break in these areas and avoids deterioration of impact resistance. Besides, the length of the grooves 27 in the longitudinal direction (L2) is not less than 55% and not greater than 65% relative to the length of the leg portions 21, 22 in the longitudinal direction (L1). This is effective in increasing the CI value of higher harmonics and ensuring the CI ratio, without overly deteriorating the CI value of the fundamental. Further, since the connecting portions 213, 223 are composed of a partial circumference of a circle and do not have a corner (a border portion) at which their width increases, the side surfaces of the leg portions do not include any area at which a stress is produced. This configuration reduces the risk of a crack or break in these areas and enhances the impact resistance.

According to the modified example described above, the connecting portions 213, 223 are provided with the closed-bottom second grooves 271 which extend in the longitudinal direction and which do not have a drive electrode, and the bridges 272 lie between the grooves 27 and the second grooves. This configuration acts to displace the nodes of higher harmonics from the areas of the vibrating portions 212, 222 where the CI value of higher harmonics is low toward the areas of the second grooves where the CI value of higher harmonics is higher. As a result, this configuration can increase the CI value of unwanted higher harmonics relative to the CI value of the fundamental required to excite the tuning fork type piezoelectric vibrator, thereby ensuring the CI ratio and suppressing higher harmonic oscillations in a more stable state.

Embodiment 2

Figure 6:
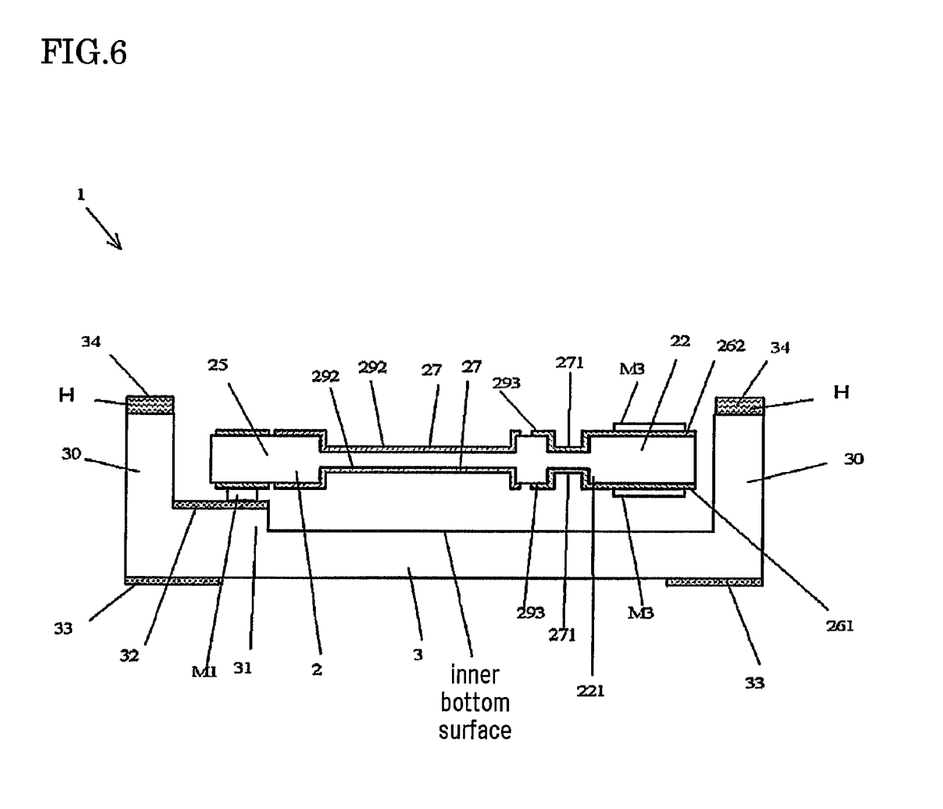
FIG. 6 is a schematic cross section of a tuning fork type quartz vibrator according to Embodiment 2.

Next, the tuning fork type quartz vibrator according to Embodiment 2 is described with reference to the drawings. A tuning fork type quartz vibrator 1 used in this embodiment is substantially similar to the one described in Embodiment 1. Hence, description of the common elements/configurations is omitted by using the same numerals/signs, and the following description focuses only on different elements/configurations.

Figure 7:
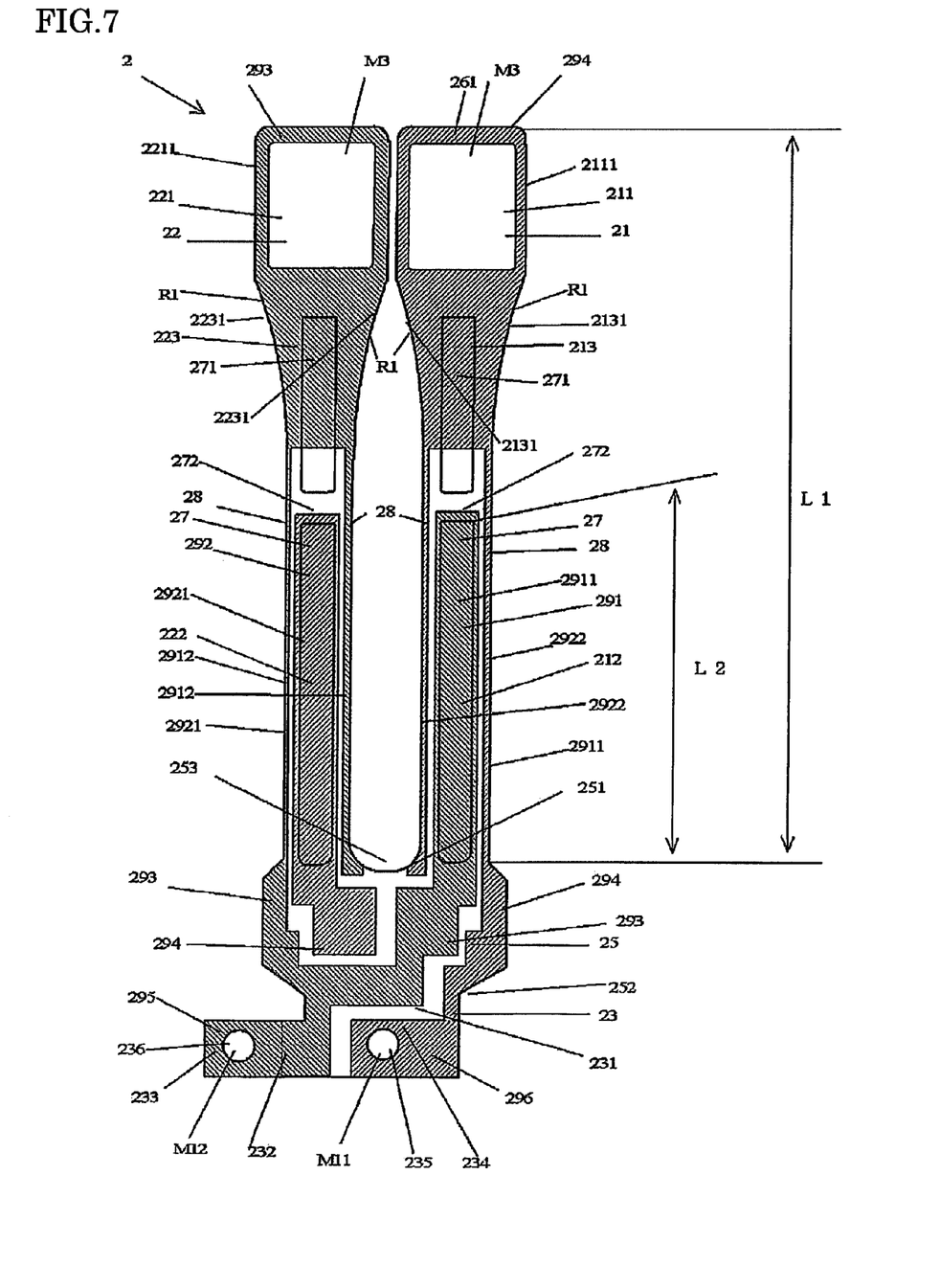
FIG. 7 is a plan view of a principle surface of a tuning fork type quartz vibration piece according to Embodiment 2.
Figure 8:
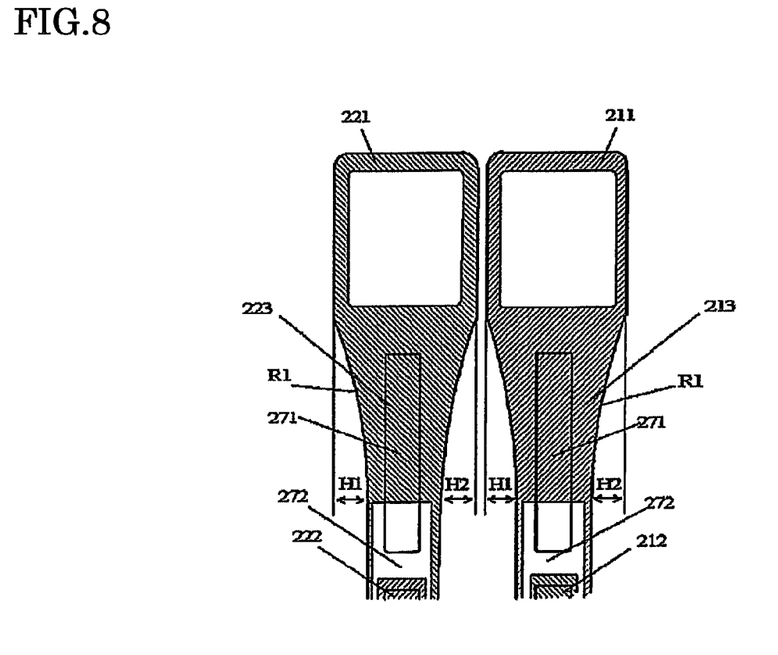
FIG. 8 is an enlarged partial plan view of the leg portions of the tuning fork type quartz vibration piece according to Embodiment 2.
Figure 9:
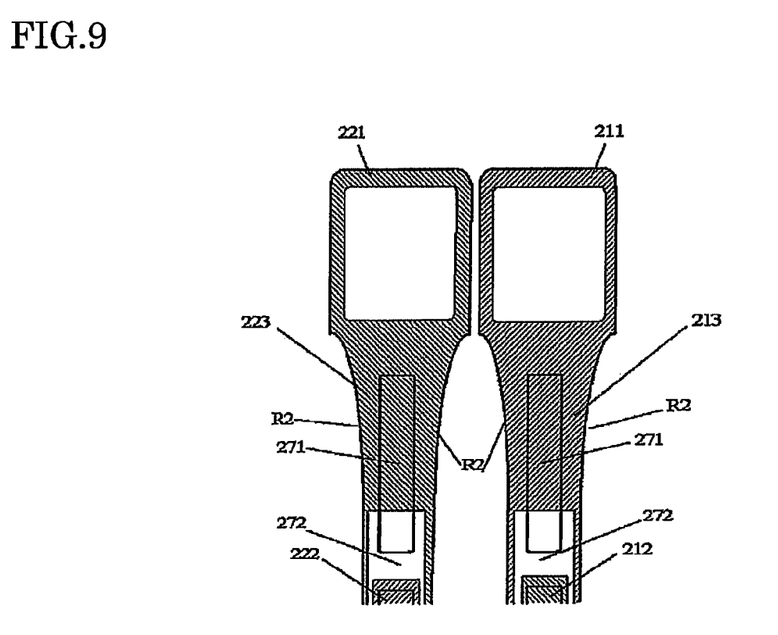
FIG. 9 is an enlarged partial plan view of the leg portions of another tuning fork type quartz vibration piece according to Embodiment 2.

FIG. 6 is a schematic cross section of a tuning fork type quartz vibrator according to Embodiment 2. FIG. 7 is a plan view of a principle surface of a tuning fork type quartz vibration piece according to Embodiment 2. FIG. 8 is an enlarged partial plan view of the leg portions of the tuning fork type quartz vibration piece according to Embodiment 2. FIG. 9 is an enlarged partial plan view of the leg portions of another tuning fork type quartz vibration piece according to Embodiment 2.

In Embodiment 1, the connecting portions 213, 223 have the widening sections 2131, 2231 whose width increases exponentially from the vibrating portions 212, 222 to the weight portions 211, 221, with the length of the widening sections 2131, 2231 being longer than their width. In Embodiment 2, the shape of the connecting portions is not limited thereto, and may be simply rounded, tapered, or stepped (in relation to their length and width). Namely, the widening sections 2131, 2231 may be composed of a partial circumference R1 as shown in FIG. 7 and FIG. 8, or may be a partial ellipse R2 whose major axis extends in the projection direction of the leg portions as shown in FIG. 9.

In the vibrating portions 212, 222, the closed-bottom second grooves 271 extend in the longitudinal direction from the tip ends of the first grooves 27, with the bridges 272 lying therebetween. The second grooves 271 extend from the tip ends of the vibrating portions 212, 222 toward the weight portions 211, 221. In the inside, the second grooves 271 are provided only with the extraction electrodes 293, 294 and not provided with a drive electrode. In this embodiment, the bridges 272 are located at the vibrating portions 212, 222, and the second grooves 271 extend in the leg portion-projecting direction from the tip ends of the vibrating portions 212, 222 to the connecting portions 213, 223. The bridges 272 are unetched areas in the tuning fork type quartz vibration piece (piezoelectric vibration substrate), and have the same thickness as areas excluding the grooves 27 and the second grooves 271 in the leg portions 21, 22. In the connecting portion 213 of the first leg portion 21 and the connecting portion 223 of the second leg portion 22, the extraction electrodes 293, 294 are formed substantially entirely on the two principle surfaces (the first principle surface 261 and the second principle surface 262) and on both of the side surfaces 28. The extraction electrodes 293, 294 are also formed inside the second grooves.

In this embodiment, the second grooves occupy only a part of the connecting portions 213, 223. However, according to the characteristics, the second grooves 271 may be extended into the weight portions 211, 221. The top surfaces of the second grooves may be free of an extraction electrode, or may be provided with extraction electrodes and adjustment metal films M3 to be described later. As far as this embodiment is concerned, at least two or more of these variations may be combined. It should be noted, however, the second grooves are not provided with a drive electrode which triggers a field-effect inside the quartz vibration piece due to close arrangement of opposite-polarity electrodes.

In the vibrating portions 212, 222, the closed-bottom second grooves 271 extend in the longitudinal direction from the tip ends of the first grooves 27, with the bridges 272 lying therebetween. The second grooves 271 extend from the tip ends of the vibrating portions 212, 222 toward the weight portions 211, 221, and are provided only with the extraction electrodes 293, 294. Owing to the presence of small-mass areas (low-rigidity areas) at the tip ends of the vibrating portions 212, 222, nodes of unwanted higher harmonics other than the fundamental can be displaced from the areas of the vibrating portions 212, 222 where the CI value of higher harmonics is low toward the areas of the connecting portions 213, 223 and the weight portions 211, 221 having the second grooves 271 where the CI value of higher harmonics is higher. Such displacement increases the CI value (series resonance resistance) of unwanted higher harmonics relative to the CI value of the fundamental required to excite the tuning fork type piezoelectric vibrator, thereby ensuring the ratio of the CI values (hereinafter called "CI ratio") and suppressing higher harmonic oscillations.

Since the bridges 272 lie between the first grooves 27 and the second grooves 271, the tip ends of the vibrating portions 212, 222 are reinforced by the bridges 272 and have an improved mechanical strength. This configuration reduces the risk of a crack or break in these areas and enhances the impact resistance. Besides, once the nodes of higher harmonics are displaced, the high-bending-stress areas between the first grooves 27 and the second grooves 271 act to prevent the displaced nodes from returning to the areas equipped with the drive electrodes. As a result, the CI ratio can be ensured in a more stable state.

The present invention can be embodied and practiced in other different forms without departing from the spirit and essential characteristics of the present invention. The above embodiments are mere examples in any respect and should not be interpreted in a limitative manner. The scope of the invention is indicated by the appended claims rather than by the foregoing description. All variations and modifications falling within the equivalency range of the appended claims are intended to be embraced therein.

INDUSTRIAL APPLICABILITY

The present invention is applicable to a piezoelectric vibration device such as a tuning fork type quartz vibrator.

DESCRIPTION OF THE REFERENCE NUMERALS 1 tuning fork type quartz vibrator
2 tuning fork type quartz vibration piece
3 base

The invention claimed is:
1. A tuning fork type piezoelectric vibration piece comprising a piezoelectric vibration substrate which has a base portion and a pair of leg portions projecting side by side from a first end face of the base portion,
  wherein a direction in which the leg portions project is taken as a longitudinal direction and a direction in which the leg portions are arranged side by side is taken as a widthwise direction, wherein each of the pair of leg portions comprises:
  a vibrating portion having a groove extending in the longitudinal direction, and a drive electrode;
  a weight portion integrally formed at a tip end side of the vibrating portion and including a part whose width is greater than that of the vibrating portion; and
  a connecting portion between the vibrating portion and the weight portion, the drive electrode in the vibrating portion comprises an inner electrode formed on an inner surface of the groove, and a side electrode formed on a side surface of the leg portion, the side electrode being opposed to the inner electrode in the widthwise direction,
  the connecting portion comprises a widening section whose width increases exponentially from the vibrating portion to the weight portion, with a length of the widening section being longer than a width thereof,
  the weight portion comprises a constant-width part whose width is fixed from a connecting position with the connecting portion, and
  the weight portion is free of a drive electrode.
2. The tuning fork type piezoelectric vibration piece according to claim 1, wherein a length of the groove is not less than 55% and not greater than 65% relative to a length of the leg portions.
3. The tuning fork type piezoelectric vibration piece according to claim 1, wherein
  the connecting portion has a second groove extending in the longitudinal direction, a bridge having neither the groove nor the second groove is provided between the groove in the vibrating portion and the second groove in the connecting portion, and a drive electrode is provided only in the groove in the vibrating portion.

4. A tuning fork type piezoelectric vibrator, wherein the tuning fork type piezoelectric vibration piece according to claim 1 is hermetically sealed inside a housing of the tuning fork type piezoelectric vibrator.

5. A tuning fork type piezoelectric vibration piece comprising a piezoelectric vibration substrate which has a base portion and a pair of leg portions projecting side by side from a first end face of the base portion,
wherein a direction in which the leg portions project is taken as a longitudinal direction and a direction in which the leg portions are arranged side by side is taken as a widthwise direction,
wherein
each of the pair of leg portions comprises:
a vibrating portion having a groove extending in the longitudinal direction, and a drive electrode;
a weight portion integrally formed at a tip end side of the vibrating portion and including a part whose width is greater than that of the vibrating portion; and
a connecting portion between the vibrating portion and the weight portion,
the drive electrode in the vibrating portion comprises an inner electrode formed on an inner surface of the groove, and a side electrode formed on a side surface of the leg portion, the side electrode being opposed to the inner electrode in the widthwise direction,
the connecting portion comprises a widening section whose width increases from the vibrating portion to the weight portion with a length of the widening section being longer than a width thereof,
a principal surface of the widening section has a shape composed of a partial circumference of a circle whose radius of curvature is equal to or greater than the width of the widening section, or a shape composed of a partial circumference of an ellipse whose major axis extends in the longitudinal direction,
the weight portion comprises a constant-width part whose width is fixed from a connecting position with the connecting portion, and
the weight portion is free of a drive electrode.

6. A tuning fork type piezoelectric vibration piece comprising a base portion and a pair of leg portions projecting side by side from a first end face of the base portion,
wherein
each of the leg portions comprises:
a vibrating portion connected with the base portion and having a drive electrode;
a weight portion arranged at a tip end side of the leg portion and having a greater width than the vibrating portion; and
a connecting portion for connecting the vibrating portion and the weight portion in such a manner as to increase a width thereof from the vibrating portion to the weight portion,
the connecting portion comprises a widening section whose width increases exponentially from the vibrating portion to the weight portion, and
the width of the connecting portion increases in such a manner as to satisfy following conditions (a) to (c) simultaneously:

(a) the widening section is composed of a smooth curve, and monotonically increases the width of the connecting portion from the vibrating portion to the weight portion;
(b) a rate of increase in the width of the connecting portion starting from a boundary between the vibrating portion and the connecting portion rises as the connecting portion is more distant from the boundary with the vibrating portion; and
(c) the rate of increase in the width of the connecting portion starts from zero at the boundary between the vibrating portion and the connecting portion.

7. A tuning fork type piezoelectric vibration piece comprising a piezoelectric vibration substrate which has a base portion and a pair of leg portions projecting side by side from a first end face of the base portion, wherein a direction in which the leg portions project is taken as a longitudinal direction and a direction in which the leg portions are arranged side by side is taken as a widthwise direction,
wherein
each of the pair of leg portions comprises:
a vibrating portion having a first groove extending in the longitudinal direction, and a drive electrode;
a weight portion integrally formed at a tip end side of the vibrating portion and including a part whose width is greater than that of the vibrating portion; and
a connecting portion between the vibrating portion and the weight portion, the drive electrode which is formed only in the vibrating portion comprises an inner electrode formed on an inner surface of the first groove, and a side electrode formed on a side surface of the leg portion, the side electrode being opposed to the inner electrode in the widthwise direction,
the connecting portion has a second groove extending in the longitudinal direction,
a bridge having neither the first groove nor the second groove is provided between the first groove in the vibrating portion and the second groove in the connecting portion, and
the bridge is located in the vibrating portion.

8. The tuning fork type piezoelectric vibration piece according to claim 7, wherein
the connecting portion comprises a widening section whose width increases exponentially from the vibrating portion to the weight portion, and
the width of the connecting portion increases in such a manner as to satisfy following conditions (a) to (c) simultaneously:
(a) the widening section is composed of a smooth curve, and monotonically increases the width of the connecting portion from the vibrating portion to the weight portion;
(b) a rate of increase in the width of the connecting portion starting from a boundary between the vibrating portion and the connecting portion rises as the connecting portion is more distant from the boundary with the vibrating portion; and
(c) the rate of increase in the width of the connecting portion starts from zero at the boundary between the vibrating portion and the connecting portion.

* * * * *